United States Patent [19]

Morgart

[11] 4,387,075
[45] Jun. 7, 1983

[54] PREANALYTICAL PROCESSING APPARATUS FOR ION EXCHANGE RESIN

[75] Inventor: James R. Morgart, Stillman Valley, Ill.

[73] Assignee: Illinois Water Treatment Company, Rockford, Ill.

[21] Appl. No.: 271,726

[22] Filed: Jun. 8, 1981

[51] Int. Cl.$^3$ ............................................. G01N 31/04
[52] U.S. Cl. ........................................ 422/50; 422/68; 422/70; 436/174; 436/178; 210/85
[58] Field of Search .......................... 422/70, 62, 50, 68; 364/497; 235/92 T, 92 MT; 73/61.1 C; 210/85, 739

[56] References Cited

U.S. PATENT DOCUMENTS

| | | | |
|---|---|---|---|
| 3,649,203 | 3/1972 | Schneider et al. | 73/61.1 C |
| 3,960,003 | 6/1976 | Beyer et al. | 73/61.1 C |
| 4,063,310 | 12/1977 | McDonald | 73/61.1 C |
| 4,199,323 | 4/1980 | Miller, Jr. et al. | 422/70 |

OTHER PUBLICATIONS

Bulletin RA-077 of Illinois Water Treatment Company, ("IWT").
Illinois Water Treatment Company "Installation and Operating Manual".
IWT Drawing No. D-2-3411.1-B.

Primary Examiner—Michael S. Marcus
Attorney, Agent, or Firm—George R. Clark; Neil M. Rose; Robert J. Fox

[57] ABSTRACT

As used to provide an effluent, from which ion-exchange capacity of a sample of a selected type of ion-exchange resin can be determined analytically, an apparatus comprises a column, which is adapted to contain the sample, a solenoid valve, which controls an effluent from an outlet of the column, a solenoid valve, which when opened allows a regenerating agent to flow into an inlet of the column, a solenoid valve, which when opened allows a rinsing agent to flow into the inlet of the column, a solenoid valve, which when opened allows an exhausting agent to flow into the inlet of the conduit, and electronic sequencing means, which operates sequentially for certain specified functions involving the solenoid valves.

8 Claims, 7 Drawing Figures

PREANALYTICAL PROCESSING APPARATUS FOR ION EXCHANGE RESIN

BACKGROUND OF THE INVENTION

This invention pertains to an apparatus, as used to provide an effluent, from which ion-exchange capacity of a sample of a selected type of ion-exchange resin can be determined analytically.

It is known for a sample of a selected type of ion-exchange resin to be regenerated, rinsed, and contacted by a salt solution, which exhausts ion-exchange capacity of the sample, so as to produce an effluent, from which ion-exchange capacity of the sample can be determined analytically, as by titration. It is conventional for such steps to be performed manually, often by firms specializing in ion-exchange resins.

As described in Bulletin RA-077 of Illinois Water Treatment Company, Rockford, Ill. 61105, a prior apparatus to perform such steps automatically had been offered commercially. The prior apparatus proved to be unreliable and thus unsuitable, primarily because of mechanical problems associated with various timing cams, which were used to actuate various mechanical switches controlling respective solenoid valves in selected sequences, one sequence for strong-acid cation-exchange resins, another sequence for strong-base anion-exchange resins, and another sequence for weak-base anion-exchange resins.

There has remained a need for a reliable apparatus to perform such steps automatically. This invention is addressed to the need.

SUMMARY OF THE INVENTION

Generally, as used to provide an effluent, from which ion-exchange capacity of a sample of a selected type of ion-exchange resin can be determined analytically, an apparatus according to this invention comprises a column, which has an inlet and an outlet, and which is adapted to contain the sample between the inlet and the outlet, a receiver, which is connected to the outlet, and a solenoid means, which is connected to and between the outlet and the receiver, which is adapted to be connected to a drain, and which is switchable between a first state wherein it allows an effluent to flow from the outlet to the receiver, and wherein it does not allow an effluent to flow from the outlet to the drain, and a second state wherein it allows an effluent to flow from the outlet to the drain, and wherein it does not allow an effluent to flow from the outlet to the receiver.

The apparatus also comprises several solenoid valves, which are connected to the inlet. One such valve is adapted to be connected to a source of a regenerating agent, which is suitable for regenerating the selected type of ion-exchange resin, so as to allow the regenerating agent to flow into the inlet when such same valve is opened, and so as not to allow the regenerating agent to flow into the inlet when such same valve is closed. Another such valve is adapted to be connected to a source of a rinsing agent, which is suitable for rinsing the selected type of ion-exchange resin in its regenerated form without reacting therewith, so as to allow the rinsing agent to flow into the inlet when such same valve is opened, and so as not to allow the rinsing agent to flow into the inlet when such same valve is closed. Another such valve is adapted to be connected to a source of an exhausting agent, which is suitable for exhausting ion-exchange capacity of the selected type of ion-exchange resin in its regenerated form, so as to allow the exhausting agent to flow into the inlet when such same valve is opened, and so as not to allow the exhausting agent to flow into the inlet when such same valve is closed.

The apparatus also comprises electronic sequencing means, which operates sequentially for a regenerating function, for a rinsing function, and for an exhausting function. In the regenerating function, which continues for a time sufficient for the sample to be regenerated completely, such same means causes the solenoid valve for the regenerating agent to be opened, while the solenoid valve for the effluent from the outlet is switched to its second state and while the solenoid valves for the rinsing and exhausting agents are closed. In the rinsing function, which continues for a time sufficient for any residue of the regenerating agent to be rinsed completely from the sample, such same means causes the solenoid valve for the rinsing agent to be opened, while the solenoid valve for the effluent from the outlet is switched to its second state and while the solenoid valves for the regenerating and exhausting agents are closed. In the exhausting function, which continues for a time sufficient for ion-exchange capacity of the sample to be exhausted completely, such same means causes the solenoid valve for the effluent from the outlet to be switched to its first state and the solenoid valve for the exhausting agent to be opened, while the solenoid valves for the regenerating and rinsing agents are closed.

When the sample has been placed in the column between the inlet and the outlet, the solenoid valve for the effluent from the outlet has been connected to the drain, other solenoid valves noted above have been connected to the sources of the respective agents, and the sequencing means has operated sequentially through the exhausting function, the receiver contains an effluent, from which ion-exchange capacity of the sample can be determined analytically.

In a preferred form of the apparatus, the solenoid valves for the respective agents comprise and are supplemented by a solenoid valve, which is adapted to be connected to a source of deionized water, a solenoid valve, which is adapted to be connected to a source of sodium sulphate, a solenoid valve, which is adapted to be connected to a source of sodium hydroxide, a solenoid valve, which is adapted to be connected to a source of hydrochloric acid, and a solenoid valve, which is adapted to be connected to a source of isopropanol.

Deionized water is suitable as a flushing agent for strong-acid cation-exchange resins, strong-base anion-exchange resins, and weak-base anion-exchange resins, and as a rinsing agent for strong-acid cation-exchange resins and strong-base anion-exchange resins, but not as a rinsing agent for weak-base anion-exchange resins, which in their regenerated forms are hydrolized to some extent by deionized water. Isopropanol is suitable as a rinsing agent for weak-base anion-exchange resins. Sodium sulphate is suitable as an exhausting agent for strong-acid cation-exchange resins, strong-base anion-exchange resins, and weak-base anion-exchange resins. Hydrochloric acid is suitable as a regenerating agent for strong-acid cation-exchange resins and weak-base anion-exchange resins. Sodium hydroxide is suitable as a regenerating agent for strong-base anion-exchange resins.

In the preferred form, the apparatus comprises a switch, which is switchable selectively among a first mode wherein the apparatus is arranged for the sample to be a sample of a selected type of strong-acid cation-exchange resin, a second mode wherein the apparatus is arranged for the sample to be a sample of a selected type of strong-base anion-exchange resin, and a third mode wherein the apparatus is arranged for the sample to be a sample of a selected type of weak-base anion-exchange resin.

When the switch is switched to each selected mode, the sequencing means operates sequentially for a flushing function, a regenerating function, a rinsing function, an exhausting function, and a flushing function. In each flushing function, which continues for a time sufficient for the column and the sample to be flushed completely, the sequencing means causes the solenoid valve for deionized water to be opened, while the solenoid valve for the effluent from the outlet is switched to its second state and while other solenoid valves noted above are closed. In the first and third modes of the switch, in the regenerating function, which continues for a time sufficient for the sample to be regenerated completely, the sequencing means causes the solenoid valve for hydrochloric acid to be opened, while the solenoid valve for the effluent from the outlet is switched to its second state and while other solenoid valves noted above are closed. In the second mode of the switch, in the regenerating function, which continues likewise, the sequencing means causes the solenoid valve for sodium hydroxide to be opened, while the solenoid valve for the effluent from the outlet is switched to its second state and while other solenoid valves noted above are closed.

In the first mode of the switch, in the rinsing function, which continues for a time sufficient for any residue of hydrochloric acid to be rinsed completely from the sample, and in the second mode of the switch, in the rinsing function, which continues for a time sufficient for any residue of sodium hydroxide to be rinsed from the sample, the sequencing means causes the solenoid valve for deionized water to be opened, while the solenoid valve for the effluent from the outlet is switched to its second state and while other solenoid valves noted above are closed. In the third mode of the switch, in the rinsing function, which continues for a time sufficient for any residue of hydrochloric acid to be rinsed completely from the sample, the sequencing means causes the solenoid valve for isopropanol to be opened, while the solenoid valve for the effluent from the outlet is switched to its second state and while other solenoid valves noted above are closed. In each such mode of the switch, in the exhausting function, which continues for a time sufficient for ion-exchange capacity of the sample to be exhausted completely, the sequencing means causes the solenoid valve for the effluent from the outlet to be switched to its first state and the solenoid valve for sodium sulphate to be opened, while other solenoid valves noted above are closed.

Preferably, the solenoid means is a solenoid valve, which has an inlet connected to the outlet of the column, which has an outlet connected to the receiver, and which has an outlet adapted to be connected to the drain. Alternatively, the solenoid means comprises a solenoid valve, which is connected to and between the outlet and the receiver so as to allow an effluent to flow from the outlet to the receiver when such same valve is opened, and so as not to allow an effluent to flow from the outlet to the receiver when such same valve is closed, and a solenoid valve, which is connected to the outlet, and which is adapted to be connected to a drain so as to allow an effluent from the outlet to flow to the drain when such same valve is opened, and so as not to allow an effluent from the outlet to flow to the drain when such same valve is closed. If so, the solenoid valves of the solenoid means are arranged for the solenoid valve connected to the receiver to be opened and the solenoid valve adapted to be connected to the drain to be closed when the solenoid means is switched to its first state and vice-versa when the solenoid means is switched to its second state.

Preferably, the apparatus comprises the sources of the respective agents, the solenoid valves for the respective agents being connected thereto, through a pump. Preferably, the sequencing means operates so as to cause the pump to operate throughout the foregoing functions of the sequencing means but not to operate otherwise.

Analogously, the apparatus of this invention can be arranged for the sample to be a sample of a selected type of weak-acid cation-exchange resin.

Advantageously, this invention eliminates mechanical problems, which were associated with such timing cams and associated mechanical components as were used in the prior apparatus mentioned above.

These and other objects, features, and advantages of this invention are evident from the following description of a preferred embodiment of this invention and an alternative embodiment of this invention.

DETAILED DESCRIPTION OF THE PREFERRED AND ALTERNATIVE EMBODIMENTS

Figure 1:
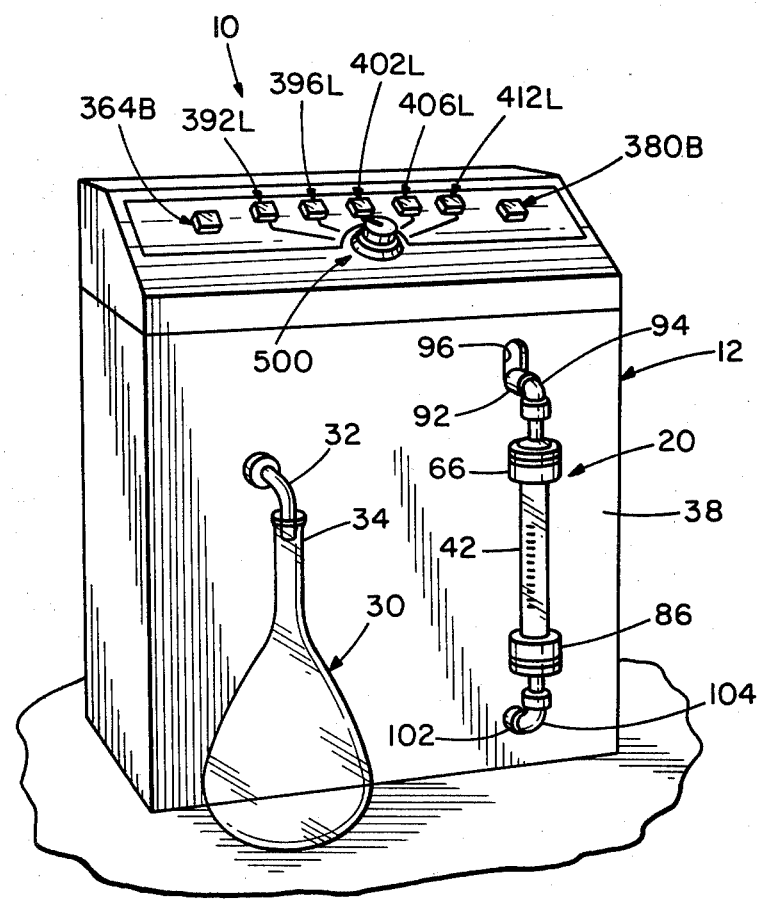
FIG. 1 is a perspective view of an apparatus embodying this invention.

As shown in FIG. 1, an apparatus 10 embodying this invention comprises a cabinet 12, which is adapted to rest on a horizontal surface, and which encloses various components described below, a column 20, which is described below, and a receiver 30, which is shown to be a one-liter volumetric flask, and which is adapted to rest on the horizontal surface. A conduit 32, which enters a neck 34 of the receiver 30 and passing into the cabinet 12 through a suitable aperture in its front wall 38. So as to allow air in the receiver 30 to be displaced by an effluent entering the receiver 30, the conduit 32 fits loosely within the neck 34. The conduit 32 may be flexible.

Figure 2:
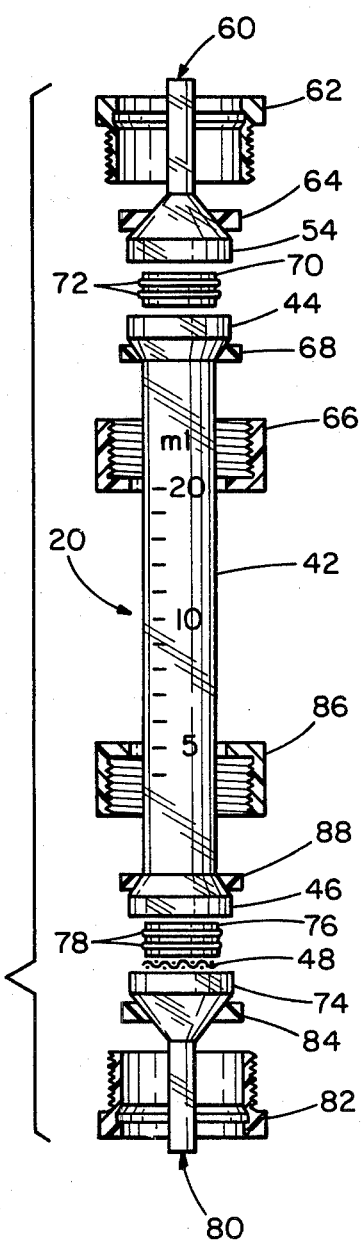
FIG. 2 is an exploded view of a column of the apparatus of FIG. 1.

As shown in FIG. 2, and also in FIG. 1, the column 20 comprises a transparent tube 42, which is graduated from its lower end in milliliters to 20 ml, and which has an annular flange 44 at its upper end and an annular flange 46 at its lower end, and which has a porous screen 48 at its lower end so as to pass fluids, and so as to retain a sample of ion-exchange resin placed in the transparent tube 42. An inlet funnel 54, which provides an inlet 60 for the column 20, is secured removably to the annular flange 44 by a threaded sleeve 62 bearing on a resilient gasket 64 around the inlet funnel 54, and by a threaded nut 66 bearing on a resilient gasket 68 around the transparent tube 42 and engaging the threaded sleeve 62. A tubular element 70, around which a pair of O-rings 72 are disposed in annular grooves formed in the tubular element 70, is inserted at its upper end in the inlet funnel 54 and at its lower end in the annular flange 44 so as to provide a watertight seal therebetween. An outlet funnel 74, in which the porous screen 48 is seated, and which provides an outlet 80 for the column 20, is secured similarly to the annular flange 46 by a threaded sleeve 82 bearing on a resilient gasket 84 around the outlet funnel 74, and by a threaded nut 86 bearing on a resilient gasket 88 around the transparent tube 42 and engaging the threaded sleeve 82. A tubular element 76, around which O-rings 78 are disposed in annular grooves formed in the tubular element 76, is inserted at its upper end in the annular flange 46 and at its lower end in the outlet funnel 74 so as to provide a watertight seal therebetween, and so as to retain the porous screen 48. A flexible conduit 92, which is connected to the inlet funnel 54 via an elbow 94, enters the cabinet 12 through a vertical slot 96 in the front wall 38. The vertical slot 96 allows the inlet funnel 54 to be elevated from the transparent tube 42 when a sample is to be placed in the transparent tube 42. A flexible conduit 102, which is connected to the outlet funnel 74 via an elbow 104, enters the cabinet 12 through an aperture in the front wall 38.

Figure 3:
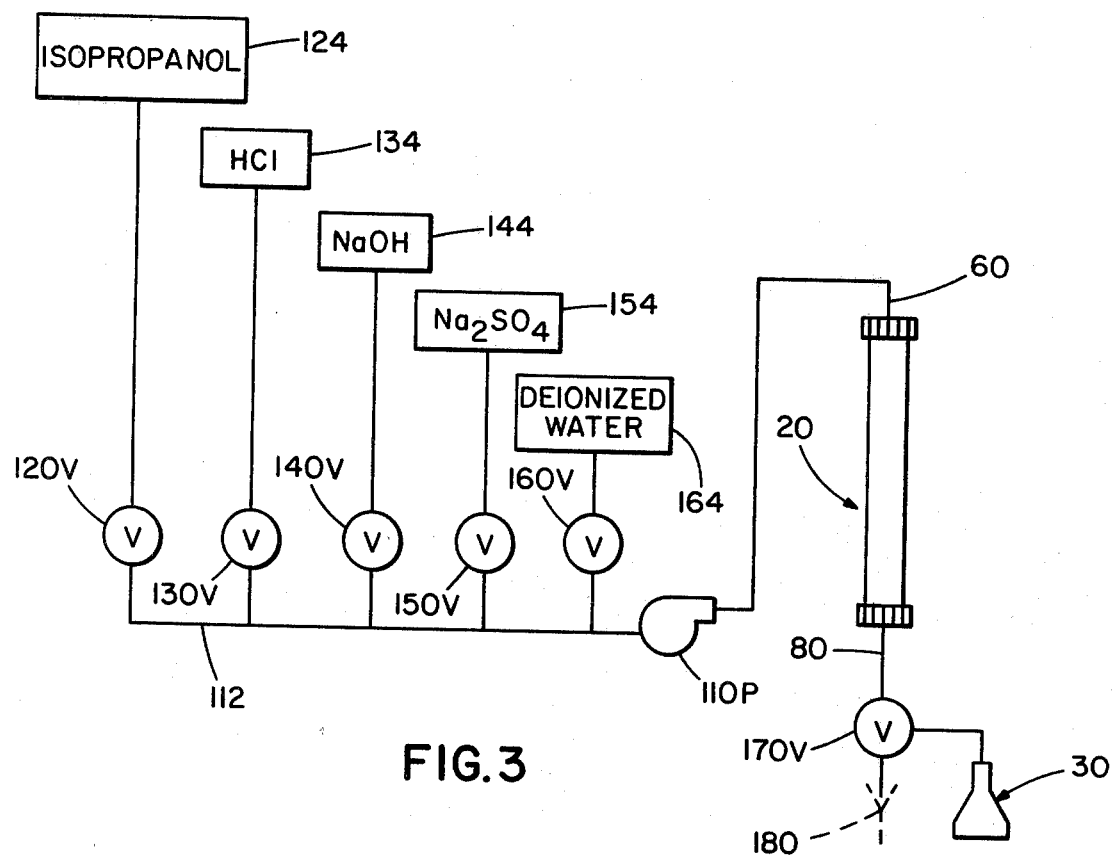
FIG. 3 is a schematic diagram of various valves and other components of the apparatus of FIG. 1 in a preferred embodiment.
Figure 4:
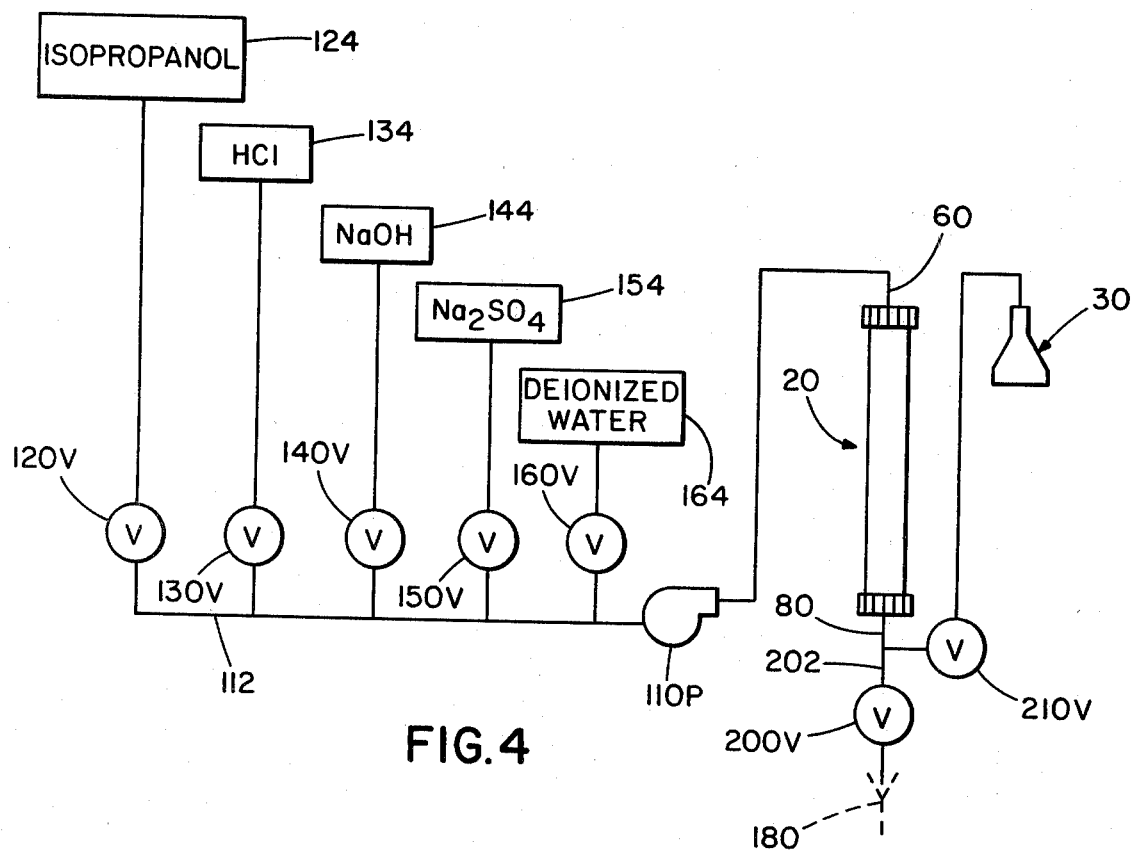
FIG. 4 is a schematic diagram of various valves and other components of the apparatus of FIG. 1 in an alternative embodiment.

As shown in a preferred embodiment in FIG. 3, and also as shown in an alternative embodiment in FIG. 4, the apparatus 10 comprises a pump 110P, which is connected at its outlet to the inlet 60 of the column 20, a solenoid valve 120V, which is connected at its outlet to the inlet of the pump 110P via a manifold 112, and which is connected at its inlet to a source 124 of isopropanol, a solenoid valve 130V, which is connected at its outlet to the inlet of the pump 110P via the manifold 112, and which is connected at its inlet to a source 134 of hydrochloric acid, HCl, 1.0 N, a solenoid valve 140V, which is connected at its outlet to the inlet of the pump 110P via the manifold 112, and which is connected at its inlet to a source 144 of sodium hydroxide, NaOH, 1.0 N, a solenoid valve 150V, which is connected at its outlet to the inlet of the pump 110P via the manifold 112, and which is connected at its inlet to a source 154 of sodium sulphate, $Na_2SO_4$, 1.0 N, and a solenoid valve 160V, which is connected at its outlet to the inlet of the pump 110P via the manifold 112, and which is connected at its inlet to a source 165 of deionized water. The solenoid valves 120V, 130V, 140V, 150V, and 160V, are arranged to be closed normally (when deenergized) and to be opened when energized.

As shown in the preferred embodiment in FIG. 3, the apparatus 10 comprises a solenoid valve 170V, which is connected at its inlet to the outlet 80 of the column 20, which is connected at a first outlet of the solenoid valve 170V to the receiver 30 and at a second outlet of the solenoid valve 170V to a drain 180, which is switchable between a first state wherein the solenoid valve 170V allows an effluent to flow from the outlet 80 of the column 20 to the receiver 30 but not to the drain 180 and a second state wherein the solenoid valve 170V allows an effluent to flow from the outlet 80 of the column 20 to the drain 180 but not to the receiver 30, and which is arranged to be switched to its second state normally (when deenergized) and to be switched to its first state when energized.

As shown in the alternative embodiment of FIG. 4, the solenoid valve 170V of the preferred embodiment in FIG. 3 is replaced by a solenoid valve 200V, which is connected at its inlet to the outlet 80 of the column 20 via a manifold 202, and which is connected at its outlet to the drain 180, and a solenoid valve 210V, which is connected at its inlet to the outlet 80 of the column 20 via the manifold 202, and which is connected to the receiver 30 via the conduit 32. The solenoid valves 200V, 210V, are arranged to be closed normally (when deenergized) and to be opened when energized.

Figure 5A:
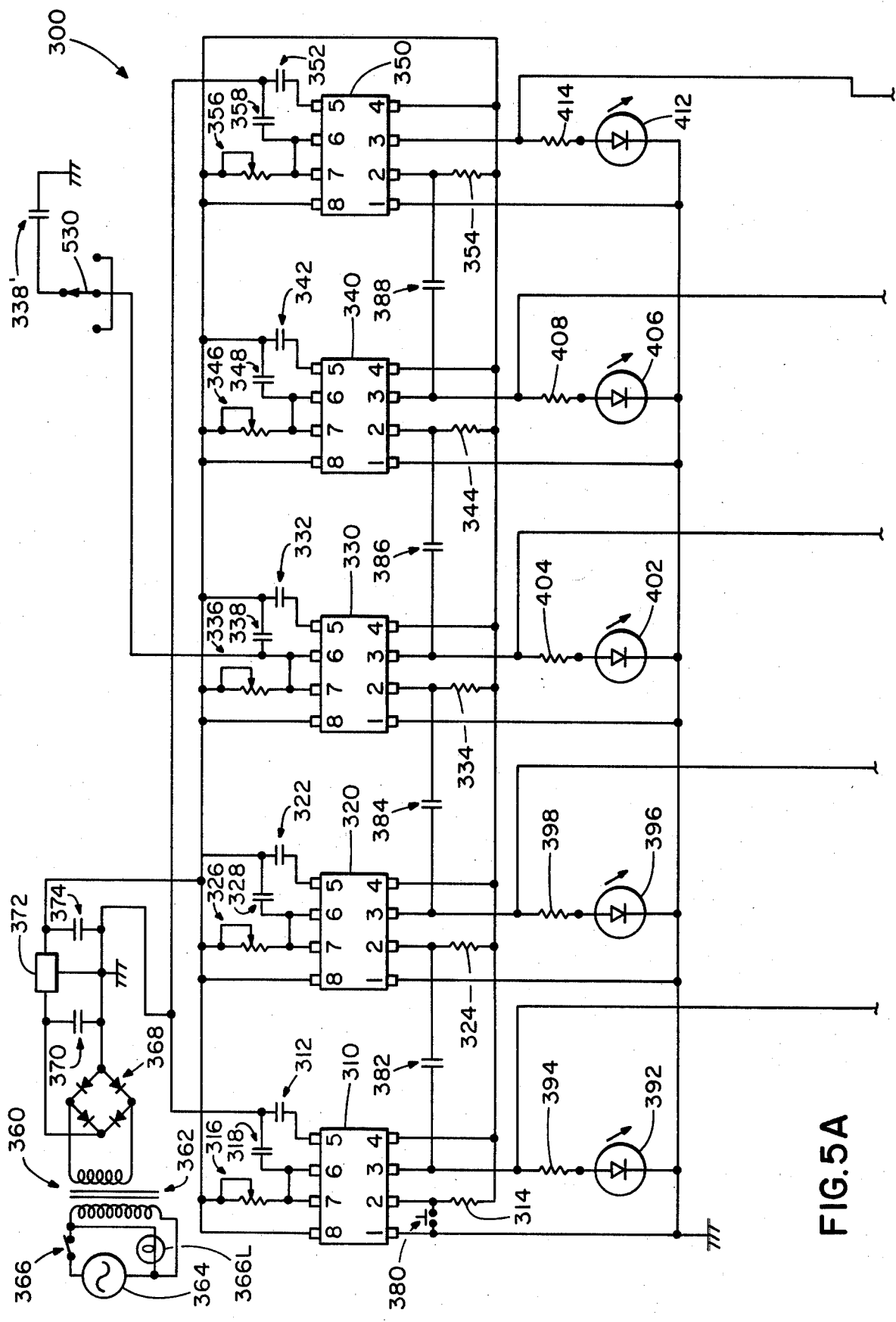
FIG. 5, which is a composite of FIGS. 5A and 5B on separate sheets, is an electrical diagram of electronic sequencing means and other electrical components of the apparatus in the preferred embodiment of FIG. 3.
Figure 5B:
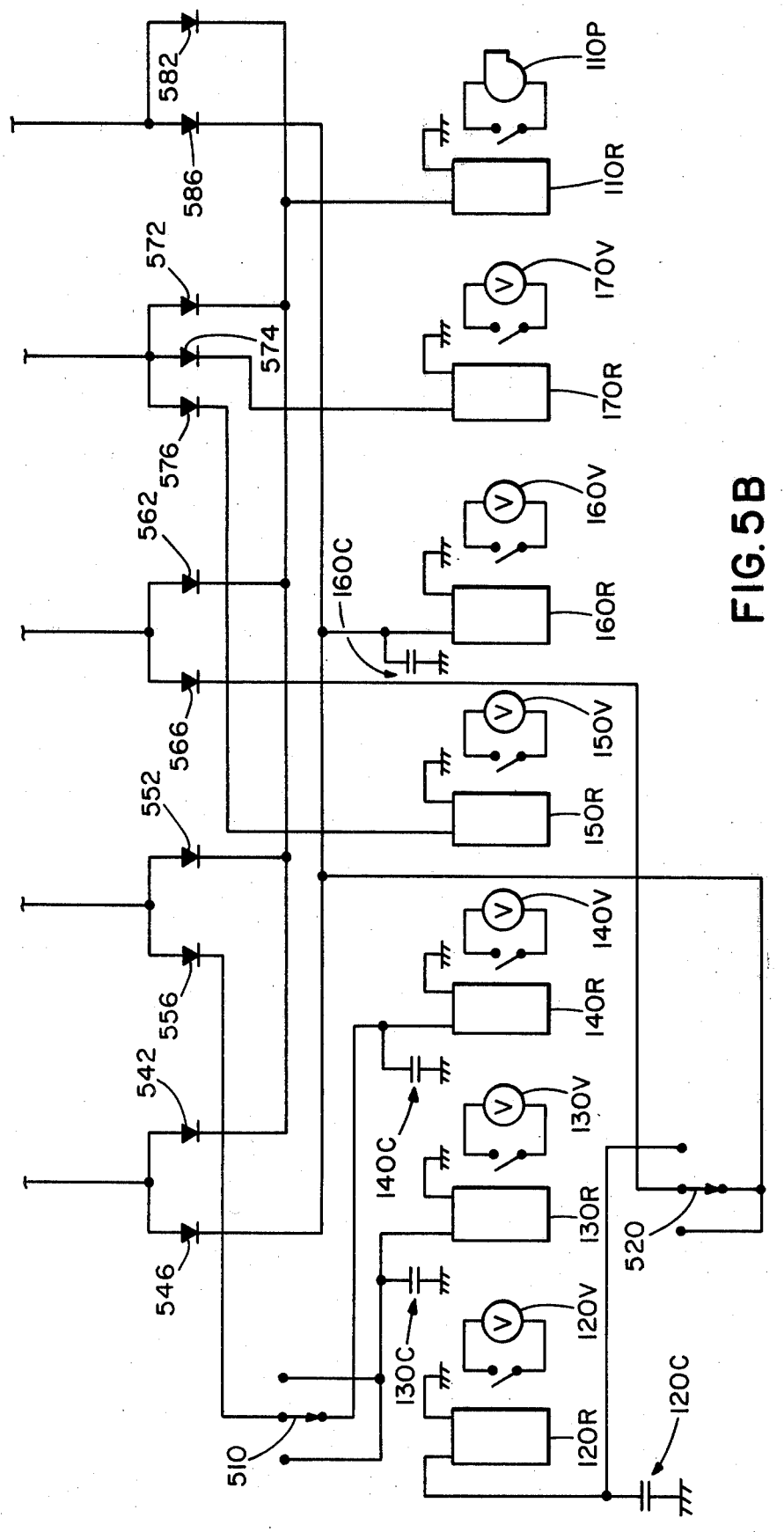
Figure 6:
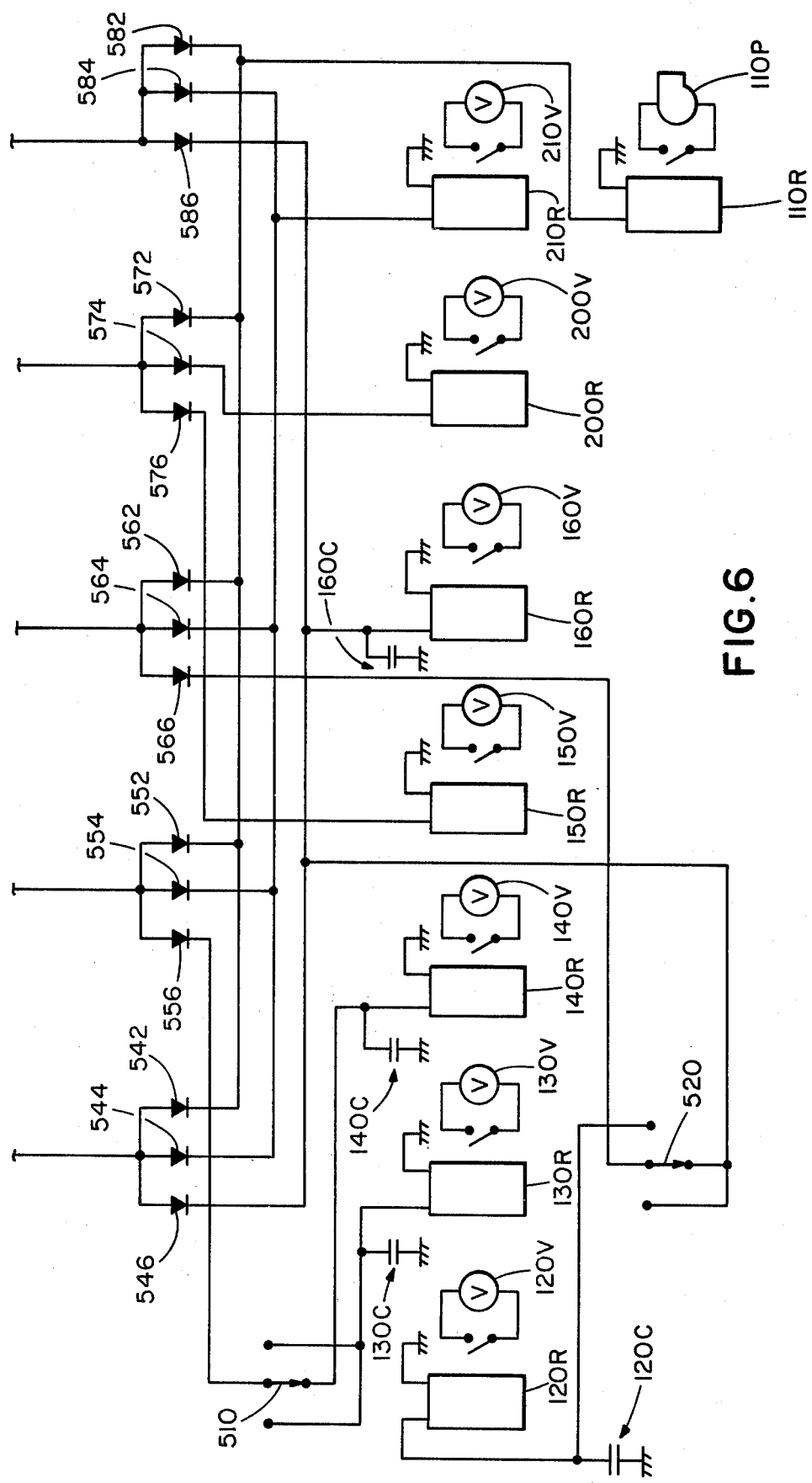
FIG. 6, which may be substituted for FIG. 5B, is an electrical diagram of certain electrical components of the apparatus in the alternative embodiment of FIG. 4. Some electrical components are common to FIGS. 5B and 6 but are connected differently in FIGS. 5B and 6.

As shown in FIG. 5B for the preferred embodiment, and also as shown in FIG. 6 for the alternative embodiment, the pump 110P is connected so as to be energized via a control relay 110R, the solenoid valve 120V connected so as to be energized via a control relay 120R, the solenoid valve 130V is connected so as to be energized via a control relay 130R, the solenoid valve 140V is connected so as to be energized via a control relay 140R, the solenoid valve 150V is connected so as to be energized via a control relay 150R, and the solenoid valve 160V is connected so as to be energized via a control relay 160R. The control relays 120R, 130R, 140R, and 160R, which are energized via a switch 500 described below, have input-filering capacitors 120C, 130C, 140C and 160C (0.01 microfarad each) connected as shown. As shown in FIG. 5B for the preferred embodiment, the solenoid valve 170V is connected so as to be energized via a control relay 170R. As shown in FIG. 6 for the alternative embodiment, the solenoid valve 200V is connected so as to be energized via a control relay 200R, and the solenoid valve 210V is connected so as to be energized via a control relay 210R.

As shown in FIG. 5A for the preferred embodiment, and also as shown therein for the alternative embodiment, the apparatus 10 comprises electronic sequencing means 300, which operates sequentially for a flushing function, a regenerating function, a rinsing function, an exhausting function, and a flushing function. In the sequencing means 300, the flushing function preceding the regenerating function is controlled by a "preflushing" timer 310. The regenerating function is controlled by a "regenerating" timer 320. The rinsing function is controlled by a "rinsing" timer 330, the exhausting function is controlled by an "exhausting" timer 340, and the flushing function following the exhausting function is controlled by a "flushing" timer 350.

Each of the respective timers 310, 320, 330, 340, 350, is a 555 timer, which may be Type LM555CH of National Semiconductor Company, 2900 Semiconductor Dr., Santa Clara, Calif. 95051. Details and applications of a 555 timer are explained in Howard M. Berlin, 555 *Timer Applications Sourcebook, with Experiments,* Blacksburg Continuing Education Series, Howard W. Sams & Co., Inc., Indianapolis, copyright 1976, wherein monostable operation of a 555 timer is explained in Chapter 2. Each 555 timer of the sequencing means 300 is connected for monostable operation.

As explained in Howard M. Berlin, op. cit., each 555 timer has a ground pin 1, a trigger pin 2, an output pin 3, a reset pin 4, a control voltage pin 5, a threshold pin 6, a discharge pin 7, and a supply voltage ($V_{cc}$) pin 8. When the trigger pin 2 receives a negative-going pulse dropping the trigger pin 2 below one-third of the supply voltage applied to the supply voltage ($V_{cc}$) pin 8, the output pin 3 is switched from a low voltage to a high voltage, which is approximately equal to the supply voltage, for a timed period determined by an R-C circuit connected to the threshold pin 6 and the discharge pin 7. After the timed period, such 555 timer is reset automatically to its standby state. So as to avoid false triggering possibilities, the reset pin 4 may be shunted to the supply voltage ($V_{cc}$) pin 8. Equivalently, respective pairs of such 555 timers may be replaced by respective 556 timers, which have fourteen pins including common supply voltage ($V_{cc}$) and ground pins.

As shown in FIG. 5A for the preferred embodiment, and also as shown therein for the alternative embodiment, the ground pins 1 are grounded to chassis ground directly, and the control voltage pins 5 are grounded to chassis ground through respective 0.01 microfarad capacitors 312, 322, 332, 342, 352. As mentioned above, the reset pins 4 are shunted to the supply voltage ($V_{cc}$) pins. Also, a supply voltage (12 VDC) is applied to the supply voltage ($V_{cc}$) pins from a power supply 360, which comprises a transformer 362 being connected on its high side to a source 364 of conventional alternating current (120 VAC) through a switch 366 and being connected on its low side to a full-wave bridge 368 so as to provide an output voltage (14 VDC) to be filtered by a capacitor 370, regulated by a voltage regulator 372, and filtered again by a capacitor 374, so as to provide the supply voltage (12 VDC) to be applied to the supply voltage ($V_{cc}$) pins 8. The switch 366 is one of a type that is depressed initially to be closed and depressed subsequentially to be opened.

As shown in FIG. 5A for the preferred embodiment, and also as shown therein for the alternative embodiment, the trigger pins 2 of the respective timers 310, 320, 330, 340, 350, are connected to the high-volage side of the power supply 360 through respective resistors 314, 324, 334, 344, 354 (22K ohms each).

The threshold pin 6 and the discharge pin 7 of the "preflushing" timer 310 are connected to an R-C circuit, which comprises a potentiometer 316 connecting these pins to the high-voltage side of the power supply 360, and which comprises a capacitor 318 (500 microfarad) connecting these pins to chassis ground. The potentiometer 316 is set manually to a resistance (approximately 1.09 megohms) causing the timed period of the "preflushing" timer 310 to be approximately 10 minutes, ±20%, as measured by a stop watch.

The threshold pin 6 and the discharge pin 7 of the "regenerating" timer 320 are connected to an R-C circuit, which comprises a potentiometer 326 connecting these pins to the high-voltage side of the power supply 360, and which comprises a capacitor 328 (500 microfarad) connecting these pins to chassis ground. The potentiometer 326 is set manually to a resistance (approximately 3.3 megohms) causing the timed period of the "regenerating" timer 320 to be approximately 30 minutes, ±5%, as measured by a stop watch.

The threshold pin 6 and the discharge pin 7 of the "rinsing" timer 330 are connected to an R-C circuit, which comprises a potentiometer 336 connecting these pins to the high-voltage side of the power supply 360, and which comprises a capacitor 338 (500 microfarad) connecting these pins to chassis ground. The potentiometer 336 is set manually to a resistance (approximately 5.5 megohms) causing the timed period of the "rinsing" timer 330 to be approximately 50 minutes, ±5%, as measured by a stop watch. Another capacitor 338' (500 microfarad) can be switched into parallel connection with the capacitor 338, in a manner described below, so as to change the timed period of the "rinsing" timer 330 to approximately 100 minutes, ±5%, as measured by a stop watch. As explained below, the shorter period is appropriate for rinsing strong-acid cation-exchange resins with deionized water and for rinsing weak-base anion-exchange resins with isopropanol, and the longer period is appropriate for rinsing strong-base anion-exchange resins with deionized water. Similarly, the timed period of the "rinsing" timer 330 can be changed to a different period of intermediate length for rinsing weak-base anion-exchange resins with distilled water, such a period of approximately 70 minutes being appropriate.

The threshold pin 6 and the discharge pin 7 of the "exhausting" timer 340 are connected to an R-C circuit, which comprises a potentiometer 346 connecting these pins to the high-voltage side of the power supply 360, and which comprises a capacitor 348 (500 microfarad) connecting these pins to chassis ground. The potentiometer 346 is set manually to a resistance (approximately 3.3 megohms) causing the timed period of the "exhausting" timer 340 to be approximately 30 minutes, ±3%, as measured by a stop watch.

The threshold pin 6 and the discharge pin 7 of the "flushing" timer 350 are connected to an R-C circuit, which comprises a potentiometer 356 connecting these pins to the high-voltage side of the power supply 360, and which comprises a capacitor 358 (500 microfarad) connecting these pins to chassis ground. The potentiometer 356 is set manually to a resistance (approximately 1.09 megohms) causing the timed period of the "flushing" timer 350 to be approximately 10 minutes, ±20%, as measured by a stop watch.

As shown in FIG. 5A for the preferred embodiment, and also as shown therein for the alternative embodiment, the trigger pin 2 of the "preflushing" timer 310 is connected to chassis ground through a momentary switch 380, which is closed manually. The trigger pin 2 of the "regenerating" timer 320 is connected to the output pin 3 of the "preflushing" timer 310 through a capacitor 382 (0.001 microfarad). The trigger pin 2 of the "rinsing" timer 330 is connected to the output pin 3 of the "regenerating" timer 320 through a capacitor 384 (0.001 microfarad). The trigger pin 2 of the "exhausting" timer 340 is connected to the output pin 3 of the "rinsing" timer 330 through a capacitor 386 (0.001 microfarad). The trigger pin 2 of the "flushing" timer 350 is connected to the output pin 3 of the "exhausting" timer 340 through a capacitor 388 (0.001 microfarad).

Hence, the respective timers 310, 320, 330, 340, 350, are cascaded. As the momentary switch 380 is closed, a negative-going pulse is applied transiently through the momentary switch 380 to the trigger pin 2 of the "preflushing" timer 310, which thus is triggered. As the timed period of the "preflushing" timer 310 concludes, a decaying voltage at the output pin 3 of the "preflushing" timer 310 applies a negative-going pulse transiently across the capacitor 382 to the trigger pin 2 of the "regenerating" timer 320, which thus is triggered. As the timed period of the "regenerating" timer 320 concludes, a decaying voltage at the output pin 3 of the "regenerating" timer 320 applies a negative-going pulse transiently across the capacitor 384 to the trigger pin 2 of the "rinsing" timer 330, which thus is triggered. As the timed period of the "rinsing" timer 330 concludes, a decaying voltage at the output pin 3 of the "rinsing" timer 330 applies a negative-going pulse transiently across the capacitor 386 to the trigger pin 2 of the "exhausting" timer 340, which thus is triggered. As the timed period of the "exhausting" timer 340 concludes, a decaying voltage at the output pin 3 of the "exhausting" timer 340 applies a negative-going pulse transiently across the capacitor 388 to the trigger pin 2 of the "flushing" timer 350, which thus is triggered.

After the "preflushing" timer 310 has been triggered, it applies high voltage at its output pin 3 for its timed period, which is signalled by a light-emitting diode 392 connected via a current-limiting resistor 394 (1K ohms) between the output pin 3 of the "preflushing" timer 310 and chassis ground. After the "regenerating" timer 320 has been triggered, it applies a high voltage at its output pin 3 for its timed period, which is signalled by a light-emitting diode 396 connected via a current-limiting resistor 398 (1K ohms) between the output pin 3 of the "regenerating" timer 320 and chassis ground. After the "rinsing" timer 330 has been triggered, it applies a high voltage at its output pin 3 for its timed period, which is signalled by a light-emitting diode 402 connected via a current-limiting resistor 404 between the output pin 3 of the "rinsing" timer 330 and chassis ground. After the "exhausting" timer 340 has been triggered, it applies a high voltage at its output pin 3 for its timed period, which is signalled by a light-emitting diode 406 connected via a current-limiting resistor 408 (1K ohms) between the output pin 3 of the "exhausting" timer 340 and chassis ground. After the "flushing" timer 350 has been triggered, it applies a high voltage at its output pin 3 for its timed period, which is signalled by a light-emitting diode 412 connected via a current-limiting resistor 414 between the output pin 3 of the "flushing" timer 350 and chassis ground.

In the preferred embodiment, and also in the alternative embodiment, the apparatus 10 comprises a switch 500, which has a first pole 510, a second pole 520, and a third pole 530, and which is switchable manually among a first mode, a second mode, and a third mode. In the first mode, the apparatus 20 is arranged for the sample of ion-exchange resin to be a sample of a selected type of strong-acid cation-exchange resin, for which deionized water is suitable as a flushing agent for the flushing function preceding the regenerating function and the flushing function following the exhausting function and as a rinsing agent for the rinsing function, for which hydrochloric acid is suitable as a regenerating agent for the regenerating function, and for which sodium sulphate is suitable as an exhausting agent for the exhausting function. In the second mode, the apparatus 20 is arranged for the sample of ion-exchange resin to be a sample of strong-base anion-exchange resin, for which deionized water is suitable as a flushing agent for the flushing function preceding the regenerating function and for the flushing function following the exhausting function and as a rinsing agent for the rinsing function, for which sodium hydroxide is suitable as a regenerating agent for the regenerating function, and for which sodium sulphate is suitable as an exhausting agent for the exhausting function. In the third mode, the apparatus 20 is arranged for the sample of ion-exchange resin to be a sample of weak-base anion-exchange resin, for which deionized water is suitable as a flushing agent for the flushing function preceding the regenerating function and for the flushing function following the exhausting function, but not as a rinsing agent for the rinsing function, for which hydrochloric acid is suitable as a regenerating agent for the regenerating function, and for which isopropanol is suitable as a rinsing agent for the rinsing function.

In the preferred embodiment, in the first, second, and third modes, the output pin 3 of the "preflushing" timer 310 is connected through a diode 542 to the control relay 110R, which controls the pump 110P, and through a diode 546 to the control relay 160R, which controls the solenoid valve 160V for deionized water. As the solenoid valve 170V is not energized, the effluent from the column 20 flows to the drain 180. Thus, in the preflushing function preceding the regenerating function, the sequencing means 300 causes deionized water to flow through the column 20 to the drain 180 for the timed period of the "preflushing" timer 310. The timed period of the "preflushing" timer 310 is sufficient for the column 20 and the sample ion-exchange resin to be flushed completely.

In the preferred embodiment, in the first and third modes, the output pin 3 of the "regenerating" timer 320 is connected through a diode 552 to the control relay 110R, which controls the pump 110P, and through a diode 556 and the first pole 510 of the switch 500 to the control relay 130R, which controls the solenoid valve 130V for hydrochloric acid. As the solenoid valve 170V is not energized, the effluent from the column 20 flows to the drain 180. In the regenerating function, the sequencing means 300 causes hydrochloric acid to flow through the column 20 to the drain 180 for the timed period of the "regenerating" timer 320. The timed period of the "regenerating" timer 320 is sufficient for the sample of ion-exchange resin to be regenerated completely.

In the preferred embodiment, in the second mode, the output pin 3 of the "regenerating" timer 320 is connected through a diode 552 to the control relay 110R, which controls the pump 110P, and through the diode 556 and the first pole 510 of the switch 500 to the control relay 140R, which controls the solenoid valve 140V for sodium hydroxide. As the solenoid valve 170V is not energized, the effluent from the column 20 flows to the drain 180. In the regenerating function, the sequencing means 300 causes sodium hydroxide to flow through the column 20 to the drain 180 for the timed period of the "regenerating" timer 320. The timed period of the "regenerating" timer 320 is sufficient for the sample of strong-base anion-exchange resin to be regenerated completely.

In the preferred embodiment, in the first mode, the output pin 3 of the "rinsing" timer 330 is connected through a diode 562 to the control relay 110R, which controls the pump 110P, and through a diode 566 and the second pole 520 of the switch 500 to the control relay 160R, which controls the solenoid valve 160V for deionized water. As the solenoid valve 170V is not energized, the effluent from the column 20 flows to the drain 180. Thus, in the rinsing function, the sequencing means 300 causes deionized water to flow through the column 20 to the drain 180 for the timed period for the "rinsing" timer 330. The timed period of the "rinsing"

timer 330 is sufficient for any residue of hydrochloric acid to be rinsed completely from the sample of strong-acid cation-exchange resin in its regenerated form.

In the preferred embodiment, in the second mode, the output pin 3 of the "rinsing" timer 330 is connected through the diode 562 to the control relay 110R, which controls the pump, and through the diode 566 and the second pole 520 of the switch 500 to the control relay 160R, which controls the solenoid valve 160V for deionized water. Via the third pole 530 of the switch 500, the capacitor 338' is switched into parallel connection with the capacitor 338. As the solenoid valve 170V is not energized, the effluent from the column 20 flows to the drain 180. Thus, in the rinsing function, the sequencing means 300 causes deionized water to flow through the column 20 to the drain 180 for the timed period of the "rinsing" timer 330. As changed by the capacitor 338, the timed period of the "rinsing" timer 330 is sufficient for any residue of sodium hydroxide to be rinsed completely from the sample of strong-base anion-exchange resin.

In the preferred embodiment, in the third mode, the output pin 3 of the "rinsing" timer 330 is connected through the diode 562 to the control relay 110R, which controls the pump 110P, and through the diode 556 and the second pole 520 of the switch 500 to the control relay 120R, which controls the solenoid valve 120V for isopropanol. As the solenoid valve 170V is not energized, the effluent from the column 20 flows to the drain 180. Thus, in the rinsing function, the sequencing means 300 causes isopropanol to flow through the column 20 to the drain 180 for the timed period of the "rinsing" timer 330. The timed period of the "rinsing" timer 330 is sufficient for any residue of hydrochloric acid to be rinsed completely from the sample of weak-base anion-exchange resin.

In the preferred embodiment, in the first, second, and third modes, the output pin 3 of the "exhausting" timer 340 is connected through a diode 572 to the control relay 110R, which controls the pump 110P, through a diode 574 to the control relay 170R, which controls the solenoid valve 170V for the effluent from the column 20, and through a diode 576 to the control relay 150R, which controls the solenoid valve 150V for sodium sulphate. Thus, in the exhausting function, the sequencing means 300 causes sodium sulphate to flow through the column 20 for the timed period of the "exhausting" timer 340. The timed period of the "exhausting" timer is sufficient for ion-exchange capacity of the sample of ion-exchange resin to be exhausted completely.

In the preferred embodiment, in the first, second, and third modes, the output pin 3 of the "flushing" timer 350 is connected through a diode 582 of the control relay 110R, which controls the pump 110P, and through a diode 586 to the control relay 160R, which controls the solenoid valve 160V for deionized water. As the solenoid valve 170V is not energized, the effluent from the column 20 flows to the drain 180. Thus, in the flushing function following the exhausting function, the sequencing means 300 causes deionized water to flow through the column 20 to the drain 180 for the timed period of the "flushing" timer 350. The timed period of the "flushing" timer 350 is sufficient for the column 20 and the sample of ion-exchange resin to be flushed completely. It is to be noted that in the first, second, and third modes, the flushing function controlled by the "flushing" timer 350 is like the flushing function controlled by the "preflushing" timer 310.

In the alternative embodiment, in the first, second, and third modes, the output pin 3 of the "preflushing" timer 310 is connected through the diode 542 to the control relay 110R, which controls the pump 110P, through a diode 544 to the control relay 210R, which controls the solenoid valve 210V between the column 20 and the drain 180, and through the diode 546 to the control relay 160R, which controls the solenoid valve 160V for deionized water. Otherwise, the flushing functions preceding the regenerating functions are like the flushing functions preceding the regenerating functions in the preferred embodiment, as described above.

In the alternative embodiment, in the first and third modes, the output pin 3 of the "regenerating" timer 320 is connected through the diode 552 to the control relay 110R, which controls the pump 110P, through a diode 554 to the control relay 210R, which controls the solenoid valve 210V between the column 20 and the drain 180, and through the diode 556 and the first pole 510 of the switch 500 to the control relay 130R, which controls the control valve 130V for hydrochloric acid. In the alternative embodiment, in the second mode, the output pin 3 of the "regenerating" timer 320 is connected through the diode 552 to the control relay 110R, through the diode 554 to the control relay 210R, and through the diode 556 and the first pole 510 of the switch 500 to the control relay 140R, which controls the solenoid valve 140V for sodium hydroxide. Otherwise, the regenerating functions are like the regenerating functions in the preferred embodiment, as described above.

In the alternative embodiment, in the first mode, the output pin 3 of the "rinsing" timer 330 is connected through the diode 562 to the control relay 110R, which controls the pump 110P, through a diode 564 to the control relay 210R, which controls the solenoid valve 210V between the column 20 and the drain 180, and through the diode 566 and the second pole 520 of the switch 500 to the control relay 160R, which controls the solenoid valve 160V for deionized water. In the alternative embodiment, in the second mode, the output pin 3 of the "rinsing" timer 330 is connected likewise, and, via the third pole 530 of the switch 500, the capacitor 338' is switched into parallel connection with the capacitor 338. In the alternative embodiment, in the third mode, the output pin 3 of the "rinsing" timer 330 is connected through the diode 562 to the control relay 110R, through the diode 564 to the control relay 210R, and through the diode 556 and the second pole 520 of the switch 500 to the control relay 120R, which controls the solenoid valve 120V for isopropanol. Otherwise, the rinsing functions are like the rinsing functions in the preferred embodiment, as described above.

In the alternative embodiment, in the first, second, and third modes, the output pin 3 of the "exhausting" timer 340 is connected through the diode 572 to the control relay 110R, which controls the pump 110P, through the diode 574 to the control relay 200R, which controls the solenoid valve 200V between the column 20 and the receiver 30, and through the diode 576 to the control relay 150R, which controls the solenoid valve 150V for sodium sulphate. Therefore, the exhausting functions are like the exhausting functions in the preferred embodiment, as described above.

In the alternative embodiment, in the first, second, and third modes, the output pin 3 of the "flushing" timer 350 is connected through the diode 582 to the control relay 110P, through a diode 584 to the control relay 210R, which controls the solenoid valve 210V between the column 20 and the drain 180, and through the diode 586 to the control relay 160R, which controls the control valve 160V for deionized water. Otherwise, the flushing functions following the exhausting functions are like the flushing functions following the exhausting functions in the preferred embodiment, as described above. Thus, in the first, second, and third modes, the flushing functions controlled by the "flushing" timer 350 are like the flushing functions controlled by the "preflushing" timer 310.

In the preferred embodiment, and also in the alternative embodiment, the pump 110P is controlled by the sequencing means 300 through the control relay 110R so as to operate throughout sequential preflushing, regenerating, rinsing, exhausting, and flushing functions controlled by the sequencing means 300 but not to operate otherwise.

In the preferred embodiment, in the first, second, and third modes, the sequencing means 300 causes the solenoid valves 120V, 130V, 140V, 150V, 160V, to be closed and the solenoid valve 170V to be switched to its second state, after the timed period of the "flushing" timer 350. In the alternative embodiment, in the first, second, and third modes, the sequencing means 300 causes the solenoid valves 120V, 130V, 140V, 150V, 160V, 200V, and 210V to be closed, after the timed period of the "flushing" timer 350.

As shown in FIG. 1, a pushbutton 366B for the switch 366, which must be closed manually to enable the apparatus 10, and a pushbutton 380B for the switch 380, which must be closed manually and momentarily to trigger the "preflushing" timer 310, and the switch 500, which must be switched manually to the proper mode for the selected type of ion-exchange resin, are mounted externally on the cabinet 12. A lamp 366L, which is connected in parallel with the high side of the transformer 362 so as to be illuminated when the switch 366 is closed but not when the switch 364 is opened, is arranged so as to be observable through the pushbutton 364B, which is translucent. The light-emitting diodes 392, 396, 402, 406, 412 are arranged so as to be observable through respective translucent lenses 392L, 396L, 402L, 406L, 412L, which are mounted externally on the cabinet 12.

Preferably, a pump operating at 60 cps and delivering 30 ml per minute is to be used for the pump 110P. Preferably, interconnecting conduits are to have inner diameters of approximately from 1.5 mm to 9.5 mm.

The apparatus 10 is designed for each sample to consist of 15 ml of the selected type of ion-exchange resin and to be topped with deionized water to a total of 20 ml in the column 20. The switch 500 is to be set to the proper mode for the selected type of ion-exchange resin. After the exhausting function, the receiver 30 contains approximately 900 ml of an effluent, from which ion-exchange capacity of the sample can be determined analytically, as by known techniques of titration.

Herein, all references to hydrochloric acid, sodium hydroxide, and sodium sulphate are to be understood to refer to aqueous solutions of suitable dilution, and all references to isopropanol are to be understood to refer to anhydrous grade of isopropanol, $CH_3CHOHCH_3$. Equivalently, sodium nitrate, potassium nitrate, or potassium sulphate may be substituted for sodium sulfate, which is preferred. Other metallic salts in aqueous solutions may be suitable. Equivalently, potassium hydroxide may be substituted for sodium hydroxide, which is preferred.

Equivalently, the sequencing means 300 may be replaced by electronic sequencing means employing digital counting circuitry or other timing circuitry, although the sequencing means 300 is preferred.

I claim:

1. Apparatus to provide an effluent, from which ion-exchange capacity of a sample of a selected type of ion-exchange resin can be determined analytically, said apparatus comprising
    (a) a column, which has an inlet and an outlet, and which is adapted to contain the sample between the inlet and the outlet,
    (b) a receiver, which is connected to the outlet,
    (c) a solenoid means, which is connected to and between the outlet and the receiver, which is adapted to be connected to a drain, which is switchable between a first state wherein the solenoid means (c) allows an effluent to flow from the outlet to the receiver but not to the drain and a second state wherein the solenoid means (c) allows an effluent to flow from the outlet to the drain but not to the receiver, and which is switched normally to its second state,
    (d) a solenoid valve, which is connected to the inlet, which is adapted to be connected to a source of a regenerating agent of a suitable type for regenerating the selected type of ion-exchange resin, so as to allow the regenerating agent to flow into the inlet when the solenoid valve (d) is opened, and so as not to allow the regenerating agent to flow into the inlet when the solenoid valve (d) is closed, and which is closed normally,
    (e) a solenoid valve, which is connected to the inlet, which is adapted to be connected to a source of a rinsing agent of a suitable type for rinsing the selected type of ion-exchange resin in its regenerated form without reacting with the selected type of ion-exchange resin in its regenerated form, so as to allow the rinsing agent to flow into the inlet when the solenoid valve (e) is opened, and so as not to allow the rinsing agent to flow into the inlet when the solenoid valve (e) is closed, and which is closed normally,
    (f) a solenoid valve, which is connected to the inlet, and which is adapted to be connected to a source of an exhausting agent of a suitable type for exhausting ion-exchange capacity of the selected type of ion-exchange resin in its regenerated form, so as to allow the exhausting agent to flow into the inlet when the solenoid valve (f) is opened, and so as not to allow the exhausting agent to flow into the inlet when the solenoid valve (f) is closed, and which is closed normally, and
    (g) electronic sequencing means, including a plurality of cascaded monostable multivibrators used as a plurality of sequencing timers, each of said monostable multivibrators having a preselected time constant, a first monostable multivibrator of said plurality being settable by manual switch means to initiate the timing sequences, at least one of said other monostable vibrators of said plurality being responsive to completion of a timing signal from said first monostable multivibrator, which operates sequentially
        (1) for a regenerating function wherein the means (g) causes the solenoid valve (d) to be opened, while the solenoid means (c) is switched to its second state, and while the solenoid valve (e) and the solenoid valve (f) are closed, the regenerating function continuing for a timed period sufficient for the sample to be regenerated completely, (2) for a rinsing function wherein the means (g) causes the solenoid valve (e) to be opened, while the solenoid means (c) is switched to its second state, and while the solenoid valve (d) and the solenoid valve (f) are closed, the rinsing function continuing for a timed period sufficient for any residue of the regenerating agent to be rinsed completely from the sample, and (3) an exhausting function wherein the means (g) causes the solenoid means (c) to be switched to its first state, and the solenoid valve (f) to be opened, while the solenoid valve (d) and the solenoid valve (e) are closed, the exhausting function continuing for a timed period sufficient for ion-exchange capacity of the sample of the selected type of ion-exchange resin in its regenerated form to be exhausted completely, whereby when the sample has been placed in the column between the inlet and the outlet, the solenoid means (c) has been connected to the drain, the solenoid valve (d) has been connected to the source of the regenerating agent, the solenoid valve (e) has been connected to the source of the rinsing agent, the solenoid valve (f) has been connected to the source of the exhausting agent, and the means (g) has operated sequentially through the exhausting function, the receiver contains an effluent, from which ion-exchange capacity of the sample can be determined analytically.

2. The apparatus of claim 1 wherein the solenoid means (c) is a solenoid valve, which has an inlet connected to the outlet of the column, which has an outlet connected to the receiver, and which has an outlet adapted to be connected to the drain.

3. The apparatus of claim 1 wherein the solenoid means (c) comprises (h) a solenoid valve, which is connected to and between the outlet and the receiver so as to allow an effluent to flow from the outlet to the receiver when the solenoid valve (h) is opened, and so as not to allow an effluent to flow from the outlet to the receiver when the solenoid valve (h) is closed, (i) a solenoid valve, which is connected to the outlet, and which is adapted to be connected to a drain so as to allow an effluent to flow from the outlet to the drain when the solenoid valve (i) is opened, and so as not to allow the effluent to flow from the outlet to the drain when the solenoid valve (i) is closed, and wherein the solenoid valve (h) and the solenoid valve (i) are arranged for the solenoid valve (h) to be opened and the solenoid valve (i) to be closed when the solenoid means (c) is switched to its first state and for the solenoid valve (h) to be closed and the solenoid valve (i) to be opened when the solenoid means (c) is switched to its second state.

4. The apparatus of claim 1 wherein the solenoid means (c) comprises (k) a solenoid valve, which is connected to and between the outlet and the receiver so as to allow an effluent to flow from the outlet to the receiver when the solenoid valve (k) is opened, and so as not to allow an effluent to flow from the outlet to the receiver when the solenoid valve (k) is closed, and (l) a solenoid valve, which is connected to the outlet, and which is adapted to be connected to a drain so as to allow an effluent to flow from the outlet to the drain when the solenoid valve (l) is opened, and so as not to allow the effluent to flow from the outlet to the drain when the solenoid valve (l) is closed, and wherein the solenoid valve (k) and the solenoid valve (1) are arranged for the solenoid valve (k) to be opened and the solenoid valve (1) to be closed when the solenoid means (c) is switched to its first state and for the solenoid valve (k) to be closed and the solenoid valve (1) to be opened when the solenoid means (c) is switched to its second state.

5. Apparatus to provide an effluent, from which ion-exchange capacity of a sample of a selected type of strong-acid cation-exchange resin, strong-base anion-exchange resin, or weak-base anion-exchange resin can be determined analytically, said apparatus comprising (a) a column, which has an inlet and an outlet, and which is adapted to contain the sample between the inlet and the outlet, (b) a receiver, which is connected to the outlet, (c) a solenoid means, which is connected to and between the outlet and the receiver, which is adapted to be connected to a drain, which is switchable between a first state wherein the solenoid valve (c) allows an effluent to flow from the outlet to the receiver but not to the drain, and a second state wherein the solenoid means (c) allows an effluent to flow from the outlet to the drain but not to the receiver, and which is switched normally to its second state, (d) a solenoid valve, which is connected to the inlet, which is adapted to be connected to a source of deionized water so as to allow deionized water to flow into the inlet when the solenoid valve (d) is opened, and so as not to allow deionized water to flow into the inlet when the solenoid valve (d) is closed, and which is closed normally, (e) a solenoid valve, which is connected to the inlet, which is adapted to be connected to a source of sodium sulphate so as to allow sodium sulphate to flow into the inlet when the solenoid valve (e) is opened, and so as not to allow sodium sulphate to flow into the inlet when the solenoid valve (e) is closed, and which is closed normally, (f) a solenoid valve, which is connected to the inlet, which is adapted to be connected to a source of sodium hydroxide so as to allow sodium hydroxide to flow into the inlet when the solenoid valve (f) is opened, and so as not to allow sodium hydroxide to flow into the inlet when the solenoid valve (f) is closed, and which is closed normally, (g) a solenoid valve, which is connected to the inlet, which is adapted to be connected to a source of hydrochloric acid so as to allow hydrochloric acid to flow into the inlet when the solenoid valve (g) is opened, and so as not to allow hydrochloric acid to flow into the inlet when the solenoid valve (g) is closed, and which is closed normally, (h) a solenoid valve, which is connected to the inlet, which is adapted to be connected to a source of isopropanol so as to allow isopropanol to flow into the inlet when the solenoid valve (h) is opened, and so as not to allow isopropanol to flow into the inlet when the solenoid valve (h) is closed, and which is closed normally, (i) a switch, which is switchable selectively among a first mode wherein the apparatus is arranged for the sample to be a sample of a selected type of strong-acid cation-exchange resin, a second mode wherein the apparatus is arranged for the sample to be a sample of a selected type of strong-base anion-exchange resin, and a third mode wherein the apparatus is arranged for the sample to be a sample of weak-base anion-exchange resin, and (j) electronic sequencing means, including a plurality of cascaded monostable multivibrators used as a plurality of sequencing timers, each of said monostable multivibrators having a preselected time constant, a first monostable multivibrator of said plurality being settable by manual switch means to initiate the timing sequences, at least one of said other monostable multivibrators of said plurality being responsive to completion of a timing signal from said first monostable multivibrator, which when the switch is switched to its first mode operates sequentially (1) for a flushing function wherein the means (j) causes the solenoid valve (d) to be opened, while the solenoid means (c) is switched to its second state and while the solenoid valve (e), the solenoid valve (f), the solenoid valve (g), and the solenoid valve (h) are closed, the flushing function (1) continuing for a time sufficient for the column containing the sample to be flushed completely, (2) for a regenerating function wherein the means (j) causes the solenoid valve (g) to be opened, while the solenoid means (c) is switched to its second state and while the solenoid valve (d), the solenoid valve (e), the solenoid valve (f), and the solenoid valve (h) are closed, the regenerating function (2) continuing for a time sufficient for the sample to be regenerated completely, (3) for a rinsing function wherein the means (j) causes the solenoid valve (d) to be opened, while the solenoid means (c) is switched to its second state and while the solenoid valve (e), the solenoid valve (f), the solenoid valve (g), and the solenoid valve (h) are closed, the rinsing function (3) continuing for a time sufficient for any residue of hydrochloric acid to be rinsed completely from the sample, (4) for an exhausting function wherein the means (j) causes the solenoid means (c) to be switched to its first state and the solenoid valve (e) to be opened, while the solenoid valve (d), the solenoid valve (f), the solenoid valve (g), and the solenoid valve (h) are closed, the exhausting function (4) continuing for a time sufficient for ion-exchange capacity of the sample in its regenerated form to be exhausted completely, and (5) for a flushing function like the flushing function (1) above, the flushing function (5) continuing for a time sufficient for the column containing the sample to be flushed completely, which operates when the switch is switched to its second mode sequentially (6) for a flushing function like the flushing function (1) above, the flushing function (6) continuing for a time sufficient for the column containing the sample to be preflushed completely, (7) for a regenerating function wherein the means (j) causes the solenoid valve (f) to be opened, while the solenoid means (c) is switched to its second state and while the solenoid valve (d), the solenoid valve (e), the solenoid valve (g), and the solenoid valve (h) are closed, the regenerating function (7) continuing for a time sufficient for the sample to be regenerated completely, (8) for a rinsing function like the rinsing function (3) above, the rinsing function (8) continuing for a time sufficient for any residue of sodium hydroxide to be rinsed completely from the sample, (9) for an exhausting function like the exhausting function (4) above, the exhausting function (9) continuing for a time sufficient for ion-exchange capacity of the sample to be exhausted completely, and

(10) for a flushing function like the flushing function (1) above, the flushing function (10) continuing for a time sufficient for the column containing the sample to be flushed completely, and which operates when the switch is switched to its third mode sequentially

(11) for a flushing function like the flushing function (1) above, the flushing function (11) continuing for a time sufficient for the column containing the sample to be flushed completely,

(12) for a regenerating function like the regenerating function (2) above, the regenerating function (12) continuing for a time sufficient for the sample to be regenerated completely,

(13) for a rinsing function wherein the means (j) causes the solenoid valve (h) to be opened, while the solenoid means (c) is switched to its second state and while the solenoid valve (d), the solenoid valve (e), the solenoid valve (f) and the solenoid valve (g) are closed, the rinsing function (13) continuing for a time sufficient for any residue of hydrochloric acid to be rinsed completely from the sample in its regenerated form,

(14) for an exhausting function like the exhausting function (4) above, the exhausting function (14) continuing for a time sufficient for ion-exchange capacity of the sample in its regenerated form to be exhaused completely, and

(15) for a flushing function like the flushing function (1) above, the flushing function (15) continuing for a time sufficient for the column containing the sample to be flushed completely, whereby when the sample being a selected type of strong-acid cation-exchange resin, strong-base anion-exchange resin or weak-base anion-exchange resin has been placed in the column between the inlet and the outlet, the solenoid means (c) has been connected to the drain, the solenoid valve (d) has been connected to the source of deionized water, the solenoid valve (e) has been connected to the source of sodium sulphate, the solenoid valve (f) has been connected to the source of sodium hydroxide, the solenoid valve (g) has been connected to the source of hydrochloric acid, the solenoid valve (h) has been connected to the source of isopropanol, the switch has been switched to a selected mode wherein the apparatus is arranged for the sample to be a sample of the selected type, and the means (j) has operated sequentially through the exhausting function, the receiver contains an effluent, from which ion-exchange capacity of the sample can be determined analytically.

6. The apparatus of claim 5 wherein the solenoid means (c) is a solenoid valve, which has an inlet connected to the outlet of the column, which has an outlet connected to the receiver, and which has an outlet adapted to be connected to the drain.

7. The apparatus of claim 5 wherein the solenoid means (c) comprises
- (k) a solenoid valve, which is connected to and between the outlet and the receiver so as to allow an effluent to flow from the outlet to the receiver when the solenoid valve (k) is opened, and so as not to allow an effluent to flow form the outlet to the receiver when the solenoid valve (k) is closed,
- (l) a solenoid valve, which is connected to the outlet, and which is adapted to be connected to a drain so as to allow an effluent to flow from the outlet to the drain when the solenoid valve (l) is opened, and so as not to allow the effluent to flow from the outlet to the drain when the solenoid valve (l) is closed, and wherein the solenoid valve (k) and the solenoid valve (l) are arranged for the solenoid valve (k) to be opened and the solenoid valve (l) to be closed when the solenoid means (c) is switched to its first state and for the solenoid valve (k) to be closed and the solenoid valve (l) to be opened when the solenoid means (c) is switched to its second state.

8. The apparatus of claim 5, 6, or 7 wherein the solenoids (d) through (h) are connected to the inlet through a pump.

* * * * *